US007769571B2

(12) United States Patent
Bowers

(10) Patent No.: US 7,769,571 B2
(45) Date of Patent: Aug. 3, 2010

(54) CONSTRAINT STABILIZATION

(75) Inventor: Kevin J. Bowers, Bridgewater, NJ (US)

(73) Assignee: D. E. Shaw Research, LLC, New York, NY (US)

( * ) Notice: Subject to any disclaimer, the term of this patent is extended or adjusted under 35 U.S.C. 154(b) by 324 days.

(21) Appl. No.: 11/865,262

(22) Filed: Oct. 1, 2007

(65) Prior Publication Data

US 2008/0082309 A1 Apr. 3, 2008

Related U.S. Application Data

(60) Provisional application No. 60/827,539, filed on Sep. 29, 2006.

(51) Int. Cl.
*G06F 17/50* (2006.01)
*G06G 7/48* (2006.01)
(52) U.S. Cl. ............................... 703/2; 703/7; 345/419
(58) Field of Classification Search .................. 703/2, 703/7; 345/419
See application file for complete search history.

(56) References Cited

U.S. PATENT DOCUMENTS 7,610,182 B2* 10/2009 Smith et al. ..................... 703/2
2006/0262114 A1* 11/2006 Leprevost ................... 345/419

OTHER PUBLICATIONS

G. Almasi, C. Archer, J. G. Castanos, et al., Design and Implementation of Message-Passing Services for the Blue Gene/L Supercomputer, *IBM J. Res. & Dev.*, 49(2-3): 393-406, 2005.
I. T. Arkin, H. Xu, K. J. Bowers, et al., Mechanism of a Na+/H+ Antiporter, *submitted*, 2006.
K. J. Bowers, Speed Optimal Implementation of a Fully Relativistic 3D Particle Push with a Charge Conserving Current Accumulate on Modern Processors, presented at 18th International Conference on the Numerical Simulation of Plasmas, Cape Cod, MA, 2003.
K. J. Bowers, R. O. Dror, and D. E. Shaw, Overview of Neutral Territory Methods for the Parallel Evaluation of Pairwise Particle Interactions, *J. Phys. Conf. Ser.*, 16: 300-304, 2005.
K. J. Bowers, R. O. Dror, and D. E. Shaw, The Midpoint Method for Parallelization of Particle Simulations, *J. Chem. Phys.*, 124: 184109, 2006.
K. J. Bowers, R. O. Dror, and D. E. Shaw, Zonal Methods for the Parallel Execution of Range-Limited N-Body Problems, *in press, J. Comput. Phys.*, 2006.
B. R. Brooks, R. E. Bruccoleri, B. D. Olafson, et al., CHARMM: A Program for Macromolecular Energy, Minimization, and Dynamics Calculations, *J. Comput. Chem.*, 4: 187-217, 1983.
C. L. Brooks, B. M. Pettit, and M. Karplus, Structural and Energetic Effects of Truncating Long Ranged Interactions in Ionic and Polar Fluids, *J. Chem. Phys.*, 83(11): 5897-5908, 1985.
F. Cappello and D. Etiemble, MPI Versus MPI+OpenMP on the IBM SP for the NAS Benchmarks, presented at ACM/IEEE SC2000 Conference, Dallas, TX, 2000.

D. A. Case, T. E. Cheatham, III, T. Darden, et al., The Amber Biomolecular Simulation Programs, *J. Comput. Chem.*, 26(16): 1668-1688, 2005.
E. Chow and D. Hysom, Assessing Performance of Hybrid MPI/OpenMP Programs on SMP Clusters, Lawrence Livermore National Laboratory UCRL-JC-143957, 2001.
T. Darden, D. York, and L. Pedersen, Particle Mesh Ewald: An N Log(N) Method for Ewald Sums in Large Systems, *J. Chem. Phys.*, 98(12): 10089-10092, 1993.
Y. Duan and P. A. Kollman, Pathways to a Protein Folding Intermediate Observed in a 1-Microsecond Simulation in Aqueous Solution, *Science*, 282(5389): 740-744, 1998.
M. Eleftheriou, B. G. Fitch, A. Rayshubskiy, et al., Scalable Framework for 3D FFTs on the Blue Gene/L Supercomputer: Implementation and Early Performance Measurements, *IBM J. Res. & Dev.*, 49(2-3): 457-464, 2005.
B. G. Fitch, A. Rayshubskiy, M. Eleftheriou, et al., Blue Matter: Strong Scaling of Molecular Dynamics on Blue Gene/L, IBM RC23888, Feb. 22, 2006.
B. G. Fitch, A. Rayshubskiy, M. Eleftheriou, et al., Blue Matter: Approaching the Limits of Concurrency for Classical Molecular Dynamics, IBM RC23956, May 12, 2006.
B. G. Fitch, A. Rayshubskiy, M. Eleftheriou, et al., Blue Matter: Strong Scaling of Molecular Dynamics on Blue Gene/L, IBM RC23688, Aug. 5, 2005.
M. Frigo and S. G. Johnson, The Design and Implementation of FFTW3, *Proceedings of the IEEE*, 93(2): 216-231, 2005.
R. S. Germain, B. Fitch, A. Rayshubskiy, et al., Blue Matter on Blue Gene/L: Massively Parallel Computation for Biomolecular Simulation, presented at 3rd IEEE/ACM/IFIP international conference on Hardware/software codesign and system synthesis (CODES+ISSS '05), New York, NY, 2005.
T. A. Halgren, MMFF VII. Characterization of MMFF94, MMFF94s, and Other Widely Available Force Fields for Conformational Energies and for Intermolecular-Interaction Energies and Geometries, *J. Comput. Chem.*, 20(7): 730-748, 1999.
G. S. Heffelfinger, Parallel Atomistic Simulations, *Comput. Phys. Commun.*, 128(1-2): 219-237, 2000.
W. L. Jorgensen, D. S. Maxwell, and J. Tirado-Rives, Development and Testing of the OPLS All-Atom Force Field on Conformational Energetics and Properties of Organic Liquids, *J. Am. Chem. Soc.*, 118(45): 11225-11236, 1996.

(Continued)

*Primary Examiner*—Thai Phan
(74) *Attorney, Agent, or Firm*—Occhiuti Rohlicek & Tsao LLP

(57) ABSTRACT

An improved constraint approach reduces the energy drift rate to acceptable levels. In an embodiment of this approach, massively parallel constrained velocity Verlet NVE (constant particle number, constant volume, constant energy) MD simulations can be run using single precision arithmetic with very low energy drift (e.g., ~1 Kelvin per microsecond simulated time) using large timesteps (e.g., 2.5 fs) for typical systems and MD force fields.

15 Claims, No Drawings

OTHER PUBLICATIONS

S. Kumar, G. Almasi, C. Huang, et al., Achieving Strong Scaling with NAMD on Blue Gene/L, presented at IEEE International Parallel & Distributed Processing Symposium, Rhodes Island, Greece, 2006.

J. Liu, J. Wu, and D. K. Panda, High Performance RDMA Based MPI Implementation over InfiniBand, presented at 17th International Conference on Supercomputing, San Francisco, CA, 2003.

J. MacKerell, A. D., D. Bashford, M. Bellott, et al., All-Atom Empirical Potential for Molecular Modeling and Dynamics Studies of Proteins, *J. Phys. Chem. B*, 102(18): 3586-3616, 1998.

P. Mark and L. Nilsson, Structure and Dynamics of Liquid Water with Different Long-Range Interaction Truncation and Temperature Control Methods in Molecular Dynamics Simulations, *J. Comput. Chem.*, 23(13): 1211-1219, 2002.

Mellanox Technologies, Mellanox IB-Verbs API (VAPI): Mellanox Software Programmer's Interface for InfiniBand Verbs, 2001.

T. Narumi, A. Kawai, and T. Koishi, An 8.61 Tflop/s Molecular Dynamics Simulation for NaC1 with a Special-Purpose Computer: MDM, presented at ACM/IEEE SC2001 Conference, Denver, Colorado, 2001.

J. Norberg and L. Nilsson, On the Truncation of Long-Range Electrostatic Interactions in DNA, *Biophys. J.*, 79(3): 1537-1553, 2000.

V. S. Pande, I. Baker, J. Chapman, et al., Atomistic Protein Folding Simulations on the Submillisecond Time Scale Using Worldwide Distributed Computing, *Biopolymers*, 68(1): 91-109, 2003.

P. M. Papadopoulos, M. J. Katz, and G. Bruno, NPACI Rocks: Tools and Techniques for Easily Deploying Manageable Linux Clusters, *Concurrency Comput. Pract. Ex.*, 15(7-8): 707-725, 2003.

M. Patra, M. Karttunen, T. Hyvönen, et al., Molecular Dynamics Simulations of Lipid Bilayers: Major Artifacts Due to Truncating Electrostatic Interactions, *Biophys. J.*, 84: 3636-3645, 2003.

J. C. Phillips, R. Braun, W. Wang, et al., Scalable Molecular Dynamics with NAMD, *J. Comput. Chem.*, 26(16): 1781-1802, 2005.

J. C. Phillips, G. Zheng, S. Kumar, et al., NAMD: Biomolecular Simulation on Thousands of Processors, presented at ACM/IEEE SC2002 Conference, Baltimore, 2002.

S. Plimpton, Fast Parallel Algorithms for Short-Range Molecular-Dynamics, *J. Comput. Phys.*, 117(1): 1-19, 1995.

S. Plimpton and B. Hendrickson, Parallel Molecular-Dynamics Simulations of Organic Materials, *Int. J. Mod. Phys. C.*, 5(2): 295-298, 1994.

S. Plimpton and B. Hendrickson, A New Parallel Method for Molecular Dynamics Simulation of Macromolecular Systems, *J. Comput. Chem.*, 17(3): 326-337, 1996.

W. R. P. Scott, P. H. Hünenberger, I. G. Tironi, et al., The GROMOS Biomolecular Simulation Program Package, *J. Phys. Chem. A*, 103(19): 3596-3607, 1999.

M. M. Seibert, A. Patriksson, B. Hess, et al., Reproducible Polypeptide Folding and Structure Prediction Using Molecular Dynamics Simulations, *J. Mol. Biol.*, 354(1): 173-183, 2005.

Y. Shan, J. L. Klepeis, M. P. Eastwood, et al., Gaussian Split Ewald: A Fast Ewald Mesh Method for Molecular Simulation, *J. Chem. Phys.*, 122: 054101, 2005.

D. E. Shaw, A Fast, Scalable Method for the Parallel Evaluation of Distance-Limited Pairwise Particle Interactions, *J. Comput. Chem.*, 26(13): 1318-1328, 2005.

M. Snir, A Note on N-Body Computations with Cutoffs, *Theor. Comput. Syst.*, 37: 295-318, 2004.

D. van der Spoel, E. Lindahl, B. Hess, et al., GROMACS: Fast, Flexible, and Free, *Journal of Computational Chemistry*, 26(16): 1701-1718, 2005.

M. Taiji, T. Narumi, Y. Ohno, et al., Protein Explorer: A Petaflops Special-Purpose Computer System for Molecular Dynamics Simulations, presented at ACM/IEEE SC2003 Conference, Phoenix, Arizona, 2003.

R. Zhou and B. J. Berne, A New Molecular Dynamics Method Combining the Reference System Propagator Algorithm with a Fast Multipole Method for Simulating Proteins and Other Complex Systems, *J. Chem. Phys.*, 103(21): 9444-9459, 1995.

R. Zhou, E. Harder, H. Xu, et al., Efficient Multiple Time Step Method for Use with Ewald and Particle Mesh Ewald for Large Biomolecular Systems, *J. Chem. Phys.*, 115(5): 2348-2358, 2001.

\* cited by examiner

CONSTRAINT STABILIZATION

CROSS-REFERENCE TO RELATED APPLICATIONS

This application claims the benefit of U.S. Provisional Application No. 60/827,539, filed Sep. 29, 2006, titled "CONSTRAINT STABILIZATION," which is incorporated herein by reference.

This application is related to U.S. Provisional Application No. 60/827,547 titled "NUMERICAL TECHNIQUES FOR DYNAMICS SIMULATION REVERSIBILITY," filed Sep. 29, 2006, and to U.S. application Ser. No. 11/865,298 titled "NUMERICAL TECHNIQUES FOR DYNAMICS SIMULATION," filed concurrently with the present application. These applications are incorporated herein by reference.

This application is also related to PCT Application No. PCT/US2006/032498, titled "ARCHITECTURES FOR COMPUTATION OF PARTICLE INTERACTIONS," filed on Aug. 18, 2006, which is incorporated herein by reference.

BACKGROUND

This document relates to constrained dynamics simulation.

In dynamics simulations, constraints are often employed on the allowable motions of the bodies being simulated. In molecular dynamics (MD) simulations, constraints may be employed to increase the size of the simulation time step without substantially impacting the accuracy of the simulation. Generally, constraints can eliminate fast vibrational degrees of freedom from a system being simulated. For example, the distance between two bonded particles is often constrained to be constant when one of the particles represents a hydrogen atom.

Ignoring the constraints, velocities and positions can be updated in a simulation using equations of motion, for example, that specify the force on each body based on its surrounding bodies. But these updated positions and velocities will not in general satisfy the constraints. One approach to introducing the constraints is to correct the positions of the bodies after an update to move the bodies to positions that would have been achieved had the constrained equations of motion been satisfied throughout the time step. An algorithm for such a correction is the SHAKE algorithm; there are other similar algorithms. In general, the SHAKE algorithm is an iterative optimization that works on a per constraint basis to move the particles incrementally to improve the matching of the constraints. Having corrected the updated positions, the computed velocities are generally then inconsistent with the positions so the velocities are updated based on the change in position in the time step. A further update of the velocities can optionally be performed to require that the velocities are essentially perpendicular to the constrained directions by removing velocity components in the constrained directions, but such a further update is not always required.

A conventional constrained NVE (constant energy) velocity Verlet dynamics simulation algorithm that takes this approach can be described by the following time step procedure (in general, in equations below the notation a_b denotes a subscript b, and the notation a^b denotes a superscript b). Let:

F(X) be a function that produces the vector of forces given the vector of positions;

X__0 and V__0 be vectors that give all the particle positions and velocities at the beginning of a timestep and xi__0 and vi__0 give the position and velocities of just particle i;

DT be the duration of the timestep;

M be the particle mass matrix (and mi the mass of particle i);

X__1 and V__1 be the positions and velocities at the end of a timestep; and

Vectors like X__1*, V_h* and so forth be computational intermediates.

In these terms, the conventional constrained NVE velocity Verlet time step involves the following procedure:

V_h*=V__0+M^−1 F(X__0) DT/2 ... half advance velocity
X__1*=X__0+V_h*DT ... advance position
+X__1=CONSTRAIN POSITIONS ... apply position constraints
+V_h=(X__1−X__0)/DT ... correct the velocities
V__1*=V_h+M^−1 F(X__1)DT/2 ... half advance velocity
V__1=CONSTRAIN VELOCITIES ... apply velocity constraints MD simulations are often implemented with double precision arithmetic in order to reduce non-physical artifacts to an acceptable level. For example, an MD simulation of an energy conserving system usually does not exactly conserve energy due in part to finite precision arithmetic. The energy will drift as a function of simulation time and the energy drift rate may be unacceptably high if a constrained MD simulation is done with single precision arithmetic.

However, many commodity computers perform single precision arithmetic significantly faster than double precision arithmetic and have limited bandwidth between memory and processor. Significant performance benefits can be realized by using single precision arithmetic due to the faster processing and lower memory bandwidth required if the energy drift can be made acceptable on constrained MD simulations.

Many MD codes implement their constraint algorithms such that round-off errors in particle position and velocity computations become directly correlated. This in turn can cause unacceptably high negative energy drift in single precision constrained MD simulations. For example, the velocity correction step, V_h=(X__1−X__0)/DT, shown above, can cause correlation and/or high energy drift.

SUMMARY

In one aspect, in general, an improved constraint approach reduces the drift rate to acceptable levels. In an embodiment of this approach, massively parallel constrained velocity Verlet NVE (constant particle number, constant volume, constant energy) MD simulations can be run using single precision arithmetic with very low energy drift (e.g., ~1 Kelvin per microsecond simulated time) using large timesteps (e.g., 2.5 fs) for typical systems and MD force fields.

In another aspect, in general, a method for dynamics simulation includes, at iterations of a dynamics simulation, computing updated states of bodies, computing quantities associated with application of constraints to the updating of the state of the bodies, and correcting the updated states of the bodies from the computed quantities. For instance this involves computing updated positions and velocities of bodies, computing quantities associated with application of constraints to the updating of the positions and velocities of the bodies, and correcting the updated positions and velocities from the computed quantities.

Aspects described in this document include one or more of the following features:

The dynamics simulation comprises a molecular dynamics (MD) simulation.

The bodies comprise atoms, or other substantially point-like entities on the scale of the simulation being performed.

Computing the quantities associated with application of the constraints includes computing quantities associated with constraint forces on the bodies.

Computing the quantities associated with application of the constraints includes computing Lagrange multipliers associated with the constraints.

Computing the quantities associated with application of the constraints includes applying an iterative procedure to compute the quantities.

Correcting the updated positions includes incrementing the updated positions and velocities of the bodies.

The method further includes grouping constraints into separate parts.

Computing the quantities associated with application of the constraints includes separately computing quantities associated with each of the separate parts of the constraints.

Separately computing quantities associated with each of the parts includes computing all Lagrange multipliers for each part in an integrated procedure.

Computing the quantities associated with application of the constraints includes computing constraint position updates and converting the constraint position update step to update velocities using the Lagrange multipliers.

Computing quantities associated with application of constraints to the updating of the state of the bodies includes replicating at least some of said computation on multiple nodes in a parallel computing system.

The method is implemented using numerical techniques described in the co-pending application titled "NUMERICAL TECHNIQUES FOR DYNAMICS SIMULATION."

The method is implemented using reversible arithmetic.

The method is used in an implementation of a simulation system described in the co-pending PCT application titled "ARCHITECTURES FOR COMPUTATION OF PARTICLE INTERACTIONS."

Eliminating the velocity correction step and merging it with the constraint position update step in MD integration algorithms.

Merging constraints into independent bundles and computing the all Lagrange multipliers for constraints in a bundle simultaneously and explicitly.

Converting the constraint position update step to update velocities using the Lagrange multipliers and then redoing the position step using the updated velocities.

Replicating a constraint calculation on multiple nodes in a parallel implementation to avoid extra interprocessor communication.

Using reversible arithmetic to reduce storage requirements for the algorithm without affecting results at all.

Techniques developed for the constraint algorithm implementation can make it possible to run unconstrained MD simulations exactly time reversibly as well in certain circumstances.

In another aspect, in general, a system implements all the steps of any of the methods set forth above. For example, a system described in co-pending PCT application titled "ARCHITECTURES FOR COMPUTATION OF PARTICLE INTERACTIONS," implements the method steps in its computational units.

In another aspect, in general, software, which may be stored on a computer readable medium, comprises instructions for causing a data processing system to perform the steps of any of the methods set forth above.

Other features and advantages of the invention are apparent from the following description, and from the claims.

DESCRIPTION

A new approach to imposing constraints can be summarized using the terminology presented above. Each constrained NVE velocity Verlet time step involves the following procedure:

V_h*=V_0+M^−1 F(X_0)DT/2 . . . half advance velocity
X_1*=X_0+V_h*DT . . . advance position
+X_1,V_h=NEW CONSTRAIN POSITIONS . . . apply position constraints
V_1*=V_h+M^−1 F(X_1)DT/2 . . . half advance velocity
V_1=CONSTRAIN VELOCITIES . . . apply velocity constraints A feature of this approach as compared to the conventional approach described earlier in this document is that in the third step, both the positions and the velocities are corrected to satisfy the constraints together, as opposed to correcting one, such as the positions, and then deriving the other, such as the velocities, from based on that correction. In this way, errors in position and in velocity, for example due to rounding using single precision arithmetic, may be less correlated than in the two-step approach conventionally used. Such correlation can be responsible for energy drift in a simulation, and therefore minimal correlation between errors in the position and velocity terms is desirable. In the new approach, the velocity update is essentially merged into the position update in a SHAKE-like algorithm.

As an example, consider two bodies that are rigidly separated at a fixed distance. The position update, disregarding the constraints, advances the positions such that they are no longer separated by the fixed distance. Using a conventional SHAKE algorithm, the positions of the bodies are incrementally corrected until the constraint is satisfied, and then the implied velocities are calculated based on the initial and final positions in the time step.

The new approach, generally, avoids a velocity correction step that is applied based on a modified position constraint step. The velocity correction is merged with position constraints. A Lagrange multiplier is introduced for each constraint. The Lagrange multiplier is iteratively computed so that for a particular value of the multiplier, incremental corrections to both the positions and the velocities of the bodies can be found. The positions themselves are not updated in the SHAKE-like iteration. Rather, incremental corrections to both position and velocity are computed based on the Lagrange multipliers, and these are applied to the positions and velocities that were updated using the unconstrained equations of motion. Essentially, an isolated Lagrange-multiplier based "side problem" is formulated to find corrections of the positions and velocities, and this problem is solved at each time step.

As an example, suppose we have five particles (i,j,k,l,m) and we want to constrain the distance between i-j to d_ij, between j-k to d_jk and between l-m to d_lm. To constrain these particles, we need to find lambda_ij, lambda_jk and lambda_lm (these are the Lagrange multipliers for each constraint) such that the update:

$$xi\_1 = xi\_1* + \text{lambda}\_ij(xi\_0 - xj\_0)mj/(mi+mj)$$

$$xj\_1 = xj\_1* - \text{lambda}\_ij(xi\_0 - xj\_0)mi/(mi+mj) + \text{lambda}\_jk(xj\_0 - xk\_0)mk/(mj+mk)$$

$$xk\_1 = xk\_1* - \text{lambda}\_jk(xj\_0 - xk\_0)mj/(mj+mk)$$

$$xl\_1 = xl\_1* + \text{lambda}\_lm(xl\_0 - xm\_0)mj/(mi+mj)$$

$$xm\_1 = xm\_1* - \text{lambda}\_lm(xl\_0 - xm\_0)mj/(mj+mk)$$

results in positions that satisfy the constraint equations:

$$|xi\_1 - xj\_1| = d\_ij$$

$$|xj\_1 - xk\_1| = d\_jk$$

$$|xl\_1 - xm\_1| = d\_lm$$

The functional form of the above update can be derived by requiring conservation of momentum and by requiring each constraint act along the line between the relevant particles. Because the constraint equations cannot be solved in a closed form for general situations, the above equations are usually solved iteratively. In the usual approach, each constraint updates the position of its associated particles in a SHAKE-like iteration. The position update for the i-j constraint is:
 . . . Solve the linearized system $$xij\_1^* = xi\_1^* - xj\_1^* \ldots \text{Current separation}$$

$$xij\_0 = xi\_0 - xj\_0 \ldots \text{Constraint direction}$$

$$\text{delta} = \frac{d\_ij^{\wedge}2 - |xij\_1^*|^{\wedge}2}{2\, xij\_0 \cdot xij\_1^*}$$

. . . Update the positions $$x1\_1^* = x1\_1^* + \text{delta}\, xij\_0\, mj/(mi+mj)$$

$$xj\_1^* = xj\_1^* - \text{delta}\, xij\_0\, mi/(mi+mj)$$

and similarly for the other constraints. (This can be obtained by assuming each constraint is independent of the other constraints, solving the linearized independent constraint equation and performing the resulting position update.) The SHAKE iteration is stopped when X__1* satisfies the constraints sufficiently. In this algorithm, the Lagrange multipliers are never explicitly computed.

In some examples of the new approach, instead of computing the updates for each constraint individually, the constraints are grouped into bundles. The bundles are such that each particle in the simulation is influenced by at most one constraint bundle. For the example, the two constraints between i-j and j-k form a bundle and the constraint between l-m forms another bundle. Thus, two constraint terms in the same bundle are coupled but two constraint terms in different bundles are independent.

In MD many constraints relate to water molecules. One example of the constraints for a water ($H_2O$) molecule are the two lengths of the hydrogen-oxygen bonds and the separation of the two hydrogen atoms (i.e., the lengths of three sides of a rigid triangle). Each water molecule forms one bundle of constraints. Similarly, each carbon bonded to three hydrogens can form a bundle. The bodies involved in different bundles do not overlap.

For each constraint bundle, the Lagrange multipliers for the constraints in that bundle are computed directly via an iterative multidimensional Newton's method. (All the constraint equations in the bundle are linearized simultaneously about the current estimate for the Lagrange multipliers and the linearized system is solved directly to yield an improved estimate of the Lagrange multipliers for the next iteration.) When the Lagrange multipliers have converged sufficiently, the iteration is stopped. Of note is that the particle positions and velocities are not modified during the solution process.

For each constraint bundle, the computed Lagrange multipliers are used to update the particle velocities which in turn are used to update the particle positions. That is, the constraint forces on the particles are computed from the Lagrange multipliers, the constraint-updated velocities are determined from the computed constraint forces, and then the position update is redone using the constraint-updated velocities. For example, for the i-j/j-k constraint bundle, the position and velocity increment would be done via:
 . . . Use the Lagrange multipliers to update the velocities $$vi\_h = vi\_h^* + (1/dt)\text{lambda}\_ij(xi\_0 - xj\_0)mj/(mi+mj)$$

$$vj\_h = vj\_h^* - (1/dt)\text{lambda}\_ij(xi\_0 - xj\_0)mi/(mi+mj) + (1/dt)\text{lambda}\_jk(xj\_0 - xk\_0)mk/(mj+mk)$$

$$vk\_h = vk\_h^* - (1/dt)\text{lambda}\_jk(xj\_0 - xk\_0)mj/(mj+mk)$$

. . . Redo the position increment $$xi\_1 = xi\_0 + vi\_h\, dt\ xj\_1 = xj\_0 + vj\_h\, dt\ xk\_1 = xk\_0 + vk\_h\, dt$$

This method can yield a number of improvements:

It avoids the velocity correction step. This reduces or substantially eliminates the correlation of the velocity error with position error. This is the main advantage of this method as this correlation causes massive cooling of single precision constrained MD simulations in practice.

Computing Lagrange multipliers directly means that position finite precision does not affect the convergence of the iteration. For example, it is possible to use higher tolerances for convergence than SHAKE because the SHAKE algorithm operates directly on the position variables.

Taking into account that constraints in a bundle are coupled gives a method which converges significantly more quickly than methods like SHAKE. It also avoids other numerical artifacts; for example, the order in which constraint terms are processed in a SHAKE style iteration affects the results (in the example, SHAKE would give slightly different answers if each SHAKE iteration processed the j-k constraint before the i-j constraint rather than vice versa).

Two other optional techniques are used to optimize the implementation, for example, when implementing this method in a parallel MD code:

Each constraint bundle calculation is performed on every node that has position and velocity update responsibility for at least one of the particles in the constraint bundle. This avoids the need for certain communications before, during and/or after the constraint algorithm.

To reduce storage requirements, rather than saving X__0 for use by the constraint algorithm, X__0 is computed from X__1* and V_h* in the constraint algorithm. So that this calculation does not cause any additional finite precision round off error, the positions increments are done in such a way that they can be undone exactly. The numerical techniques used for this can also be applied to run an unconstrained MD simulation exactly time reversibly.

There are many integration schemes similar to these. These schemes may use momentum instead of velocity, use subtle rearrangement of the above steps, use of different force functions on different time steps, use thermostat algorithms to maintain constant temperature, use barostat algorithms to maintain constant pressure, however none of these details are particularly relevant to constraint stabilization but the constraint stabilization technique applies to these more elaborate integration schemes.

In an example of the techniques described above, a system for dynamics simulation includes stored data characterizing one or more groups of constraints associated with corresponding groups of bodies of a dynamics simulation. For example, this data may be static for the duration for the simulation. The system also includes stored data characterizing states of the bodies, such as the position and velocity of each body. The system includes one or more processing elements. Each of the processing elements is configured to access the states of the bodies, update the states of bodies (including computing updated positions and velocities of the bodies), access the groups of constraints associated with the groups of bodies, compute quantities associated with application of the groups of constraints to the updating of the states of the bodies, and correct the updated states of the bodies (including correcting the updated positions and velocities of the bodies from the computed quantities). As a specific example, the processing elements can correspond to the nodes of a distributed system as described in the co-pending PCT application titled "ARCHITECTURES FOR COMPUTATION OF PARTICLE INTERACTIONS."

The approaches described above can be implemented in hardware, in software, or in a combination of hardware and software. The software can include instructions stored on a machine-readable medium for causing digital processors to execute steps of the methods. Hardware can include general purpose and/or special-purpose circuitry.

Other embodiments are within the scope of the following claims.

What is claimed is:

1. A method for dynamics simulation comprising:
    at iterations of a dynamics simulation
        computing updated states of bodies, including computing updated positions and velocities of the bodies,
        computing quantities associated with application of constraints to the updating of the states of the bodies, and
        correcting the updated states of the bodies, including correcting the updated positions and velocities of the bodies from the computed quantities.

2. The method of claim 1 wherein the dynamics simulation comprises a molecular dynamics (MD) simulation.

3. The method of claim 1 wherein the bodies comprise substantially point-like entities on the scale of the simulation.

4. The method of claim 1 wherein computing the quantities associated with application of the constraints includes computing quantities associated with constraint forces on the bodies.

5. The method of claim 1 wherein computing the quantities associated with application of the constraints includes computing Lagrange multipliers associated with the constraints.

6. The method of claim 1 wherein computing the quantities associated with application of the constraints includes applying an iterative procedure to compute the quantities.

7. The method of claim 1 wherein correcting the updated positions includes incrementing the updated positions and velocities of the bodies.

8. The method of claim 1 further comprising grouping constraints into separate parts.

9. The method of claim 8 wherein computing the quantities associated with application of the constraints includes separately computing quantities associated with each of the separate parts of the constraints.

10. The method of claim 9 wherein separately computing quantities associated with each of the parts includes computing all Lagrange multipliers for each part in an integrated procedure.

11. The method of claim 1 wherein computing the quantities associated with application of the constraints includes computing constraint position updates and converting the constraint position update step to update velocities using the Lagrange multipliers.

12. The method of claim 1 wherein computing quantities associated with application of constraints to the updating of the state of the bodies includes replicating at least some of said computation on multiple nodes in a parallel computing system.

13. The method of claim 1 implemented using reversible arithmetic.

14. Software stored on a computer-readable medium comprising instructions for causing a processor to:
    compute updated states of bodies at an iteration of a dynamics simulation, including computing updated positions and velocities of the bodies,
    compute quantities associated with application of constraints to the updating of the states of the bodies; and
    correct the updated states of the bodies, including correcting the updated positions and velocities of the bodies from the computed quantities.

15. A system for dynamics simulation comprising:
    a storage for data characterizing one or more groups of constraints associated with corresponding groups of bodies of a dynamics simulation;
    a storage for data characterizing states of the bodies; and
    a processing element configured to
        access the states of the bodies,
        update the states of bodies, including computing updated positions and velocities of the bodies,
        access the groups of constraints associated with the groups of bodies,
        compute quantities associated with application of the groups of constraints to the updating of the states of the bodies, and
        correct the updated states of the bodies, including correcting the updated positions and velocities of the bodies from the computed quantities.

* * * * *